US006932985B2

(12) United States Patent
Rodriguez-Kabana

(10) Patent No.: US 6,932,985 B2
(45) Date of Patent: *Aug. 23, 2005

(54) AZIDE METHOD AND COMPOSITION FOR CONTROLLING DELETERIOUS ORGANISMS

(75) Inventor: Rodrigo Rodriguez-Kabana, Auburn, AL (US)

(73) Assignee: Auburn University, Auburn University, AL (US)

(*) Notice: Subject to any disclaimer, the term of this patent is extended or adjusted under 35 U.S.C. 154(b) by 136 days.

This patent is subject to a terminal disclaimer.

(21) Appl. No.: 10/268,050

(22) Filed: Oct. 8, 2002

(65) Prior Publication Data

US 2003/0082242 A1 May 1, 2003

Related U.S. Application Data

(63) Continuation-in-part of application No. 09/974,288, filed on Oct. 9, 2001, now Pat. No. 6,878,389.
(60) Provisional application No. 60/238,943, filed on Oct. 10, 2000.

(51) Int. Cl.$^7$ .................. A01N 59/00; A01N 33/02; A01N 33/04; A01N 33/08; A01N 33/26
(52) U.S. Cl. .................. 424/719; 424/600; 424/682; 424/722; 424/725; 504/103; 504/111; 504/188; 504/362; 504/364; 514/2; 514/8; 514/12; 514/13; 514/18; 514/21; 514/150; 514/151; 514/400; 514/419; 514/423; 514/556; 514/561; 514/562; 514/563; 514/564; 514/565; 514/567; 514/579; 514/649; 514/663; 514/667; 514/668; 514/669; 514/670; 514/970; 514/974
(58) Field of Search .................. 424/600, 682, 424/719, 722, 725; 504/103, 111, 188, 362, 364; 514/2, 8, 12, 13, 18, 21, 150, 151, 400, 419, 423, 556, 561–565, 567, 579, 649, 663, 667, 668, 669, 670, 970, 974, 671, 973

(56) References Cited

U.S. PATENT DOCUMENTS

| 1,819,399 A | 8/1931 | Wesenberg |
| 3,376,126 A | 4/1968 | McConnell et al. |
| 3,376,127 A | 4/1968 | McConnell et al. |
| 3,583,987 A | 6/1971 | Berrer et al. ............ 260/249.6 |
| 3,771,994 A | 11/1973 | McConnell et al. .......... 71/111 |
| 3,812,254 A | 5/1974 | McConnell ................ 424/226 |
| 3,880,646 A | 4/1975 | McConnell et al. .......... 71/111 |
| 4,132,780 A | 1/1979 | McConnell ................ 424/127 |
| 4,555,262 A | * 11/1985 | Thummel et al. ........... 504/214 |
| 5,185,264 A | 2/1993 | Makela ..................... 436/18 |

FOREIGN PATENT DOCUMENTS

| EP | 0 102 924 A2 | 8/1983 |
| JP | 09-227315 | 2/1997 |
| JP | 09-095402 | 8/1997 |
| JP | 10-146150 | 2/1998 |
| JP | 10-117662 | 12/1998 |
| JP | 11-209210 | 3/1999 |
| JP | 11-199416 | 7/1999 |

OTHER PUBLICATIONS

Derwent abstract, accession No. 1998–002870, abstracting JP 09–269326 (1998).*

Chalfant, et al., "Reflective Film Mulches, Millet Barriers, and Pesticides: Effects on Watermelon Mosaic Virus, Insects, Nematodes, Soil–borne Fungi, and Yield of Yellow Summer Squash," *J. Amer. Soc. Hort. Sci.*, 102(1):11–15 (1977).

Hughes & Welch, "Potassium Azide as a Nitrification Inhibitor," *Agronomy Journal*, vol. 62:595–599, (Sep.–Oct. 1970).

Bradbury, et al., "The nematicidal Properties of Azides," *Ann. Appl. Biol.* 45(2):241–250 (1957).

JP 09269326, "Stable liquid immuno–agglutination reagent," Oct. 14, 1997 (Abstract).

EPO Search Report for corresponding application EP 019776772.

Office Action for co–pending U.S. Appl. No. 10/268,049, mailed May 4, 2004.

Office Action for co–pending U.S. Appl. No. 09/974,288, mailed Mar. 26, 2003.

Office Action for co–pending U.S. Appl. No. 09/974,288, mailed Feb. 10, 2004.

Advisory Action for co–pending U.S. Appl. No. 09/974,288, mailed May 20, 2004.

Patent Abstracts of Japan, Publication No. 09–5402 "Method for Preventing Crop Injury of Azide Compound and Preventing Agent Therefor" Apr. 8, 1997; abstract and computer translation.

Patent Abstracts of Japan, Publication No. 09–227315 "Growth of Useful Plant and Soil Treating Agent for Controlling Damage by Soil Propagating Virus" Sep. 2, 1997; abstract and computer translation.

(Continued)

*Primary Examiner*—John Pak
(74) *Attorney, Agent, or Firm*—Knobbe Martens Olson & Bear LLP

(57) ABSTRACT

Disclosed is both a method and composition for controlling deleterious organisms, such as insects, nematodes and weeds by applying a compound comprised of a liquid medium comprising azide and amine. The azide can be selected from the group consisting of sodium azide and potassium azide or a combination of the two. The composition provides an effective pesticide, without causing significant harm to the environment. The composition may be applied to soil to control a population of a deleterious organism.

27 Claims, 9 Drawing Sheets

OTHER PUBLICATIONS

Patent Abstracts of Japan, Publication No. 10–117662 "Treatment of Soil to Remove Pest of Soil" May 12, 1998; abstract and computer translation.

Patent Abstracts of Japan, Publication No. 10–146150 "Growth of Useful Plant and Soil Treating Agent for Controlling Soil Insect Pest" Jun. 2, 1998; abstract and computer translation.

Patent Abstracts of Japan, Publication No. 11–199416 "Granular Soil Treatment Agent for Controlling Organism" Jul. 27, 1999; abstract and computer translation.

Patent Abstracts of Japan, Publication No. 11–209210 "Prevention of Chemical Injury by Azide Compound" Aug. 3, 1999; abstract and computer translation.

* cited by examiner

AZIDE METHOD AND COMPOSITION FOR CONTROLLING DELETERIOUS ORGANISMS

RELATED APPLICATIONS

This application is a continuation-in-part of application Ser. No. 09/974,288, filed on Oct. 9, 2001 now U.S. Pat. No. 6,878,389, which claims the benefit of provisional Application No. 60/238,943, filed on Oct. 10, 2000, the entire teachings of both of which are incorporated herein by reference.

BACKGROUND OF THE INVENTION

The present invention relates generally to the fields of biology and agriculture and more particularly to compositions and methods for use as pesticides and herbicides.

The control of insects, plant pathogens, nematodes and weeds is of central importance to the agriculture industry. In particular, the substantial reduction or elimination of nematode populations in soils is critical to initial plant growth, productivity and life span. Pathogenic fungi and nematodes develop on the extensive root systems of both annual and perennial crops, damaging them severely. Moreover, they persist in the soil after crop removal and need to be eliminated before replanting of new crops.

Approaches which have been used successfully to combat plant pathogens and nematodes have been crop rotation, fallowing for at least four years, use of pathogen and nematode-resistant crops and soil fumigation. Resistance to plant pathogens and nematodes is available only in a few crops, and resistant cultivars may not be developed in the foreseeable future for many crops of significant commercial interest. Therefore, soil fumigation remains the best alternative for control of plant pathogens and nematodes.

Methyl bromide ($CH_3Br$) is the most widely used and most universal fumigant in the world. It is used extensively for soil fumigation, as a commodity quarantine treatment (export and imports) to control a variety of pests on numerous crops, and as a structural fumigant for wood destroying pests.

Methyl bromide (hereinafter referred to as "MBr") is categorized as an ozone depleting chemical with an ozone depleting potential (ODP) of greater than 0.2 compared to trichlorofluoromethane (cfc 11), a refrigerant used as a reference gas having an ODP of 1.

Evidence on the loss of MBr to the atmosphere after soil fumigation indicates that of the total amount applied to the soil for fumigation, approximately 87% is lost to the atmosphere within seven days. On reaching the stratosphere MBr undergoes photo-oxidation, releasing bromine atoms, which enter the ozone depletion cycle. MBr loss from fumigated soils is further supported by studies which indicated a loss of as much as 70% of the applied MBr to the atmosphere through the tarp and after the tarp is removed.

As currently available alternatives to MBr are less effective and/or more expensive, the removal of MBr will be very costly. Annual losses to U.S. producers and consumers is estimated to be in the region of 1.5 billion dollars. This figure does not account for the losses due to post harvest quarantine structural fumigation losses. MBr removal would most adversely affect such commodities as tomatoes, strawberries, peppers, melons and ornamentals. The loss of MBr would thus be extremely costly to both agricultural producers and consumers as well as having a substantial impact on the U.S. economy. Nonetheless, it is the general consensus of those working in the field that no approach is currently available that will achieve the same level of broad-spectrum pest management as MBr; chemical and non-chemical approaches that are available can provide some level of agricultural pest management, but generally with narrower activity and lower crop yields and quality. Therefore, there is clearly a need for alternatives to MBr.

Various azide formulations have also been considered for controlling populations of deleterious organisms. For example, sodium or potassium azide can dissociate to form hydrazoic acid, which can destroy or inhibit many deleterious organisms. However, it has been difficult to appropriately formulate an azide composition which effectively provides an appropriate balance of controlling deleterious organisms, while not impairing beneficial organisms.

SUMMARY OF THE INVENTION

The present invention provides both compositions and methods for controlling a population of deleterious organisms in soil without causing significant harm to environment. The deleterious organisms that are the target of this invention include any pests, such as, for example, insects, fungi, nematodes, weeds and any other organism that may adversely affect agricultural endeavors. Such deleterious organisms may be controlled by applying an effective amount of an azide to a soil. A dispersal medium containing an azide can be applied to an environmental system to control a population of deleterious organisms. For example, an aqueous solution containing an azide may be applied to soil, whereby a population of target pest organisms within the soil is controlled. Application of the liquid may include applying to a soil an amount of azide effective in controlling the population of one or more targeted pests. The azide contained within the liquid may be in the form of ionic azide ($N_3^-$) and may be derived from any appropriate azide compound. For example, the azide may be sodium azide, potassium azide or a combination of both sodium and potassium azide. Sodium azide is most preferred for use in accordance with this invention.

The azide compositions of this invention contain an amine selected from group consisting of primary, secondary and tertiary aryl or alkyl amines, and mixtures thereof. Exemplary amines include ethanolamine, butylamine, diethylamine, dimethylamine, phenylethylamine, and mixtures thereof. Ethanolamine is most preferred for use in accordance with this invention.

The azide compositions can further include one or more additives such as detergents, pH buffering agents, colorants, proteins, or a combination thereof. A detergent (preferably, sodium lauryl sulfate) may also function as a wetting agent thereby improving the delivery of the liquid composition of the present invention to the soil.

The azide compositions can further contain additives to maintain the pH of the liquid medium above about 7.0. The alkalinity can be achieved by an organic or inorganic pH buffering agent, the addition of hydroxyl ions or a combination thereof.

The composition of the present invention can serve generally as a pesticide. The composition can be used more specifically as an herbicide, an insecticide, a fungicide and/or a nematocide or a combination thereof, depending upon the needs of the user to control these deleterious organisms.

A given soil also contains numerous beneficial organisms. For example, microbivorous nematodes (also known as saprophagous) are beneficially involved in organic matter transformations in soil, resulting in improvements and long-term maintenance of soil fertility and soil health. The azide formulations of the present invention eliminate or control deleterious organisms, but do not unduly negatively impact beneficial organisms, due to the selectivity of the azide, its concentration and/or its method of application.

The present invention also encompasses a kit for preparing a pesticidal composition, comprising an azide and an amine selected from group consisting of primary, secondary and tertiary aryl or alkyl amines, and mixtures thereof, and instructions for preparing the pesticidal composition and applying the pesticidal composition to an environmental system, such as, for example, soil, to control a population of a targeted deleterious organism therein. The kit can further comprise one or more additives such as, but not limited to, a detergent, a protein, and a pH buffering agent or any combination thereof.

The invention also encompasses azide-containing solutions that may be diluted in a liquid medium and applied to an environmental system, such as, for example, soil, in order to control deleterious organisms contained therein.

The invention further provides agricultural systems comprising an azide for controlling a population of deleterious organisms and one or more other components such as, for example, a fertilizer to promote crop growth.

Additional objects and aspects of the present invention will become more apparent upon review of the detailed description set forth below when taken in conjunction with the accompanying figures, which are briefly described as follows.

DETAILED DESCRIPTION OF THE DRAWINGS

Figure 1:
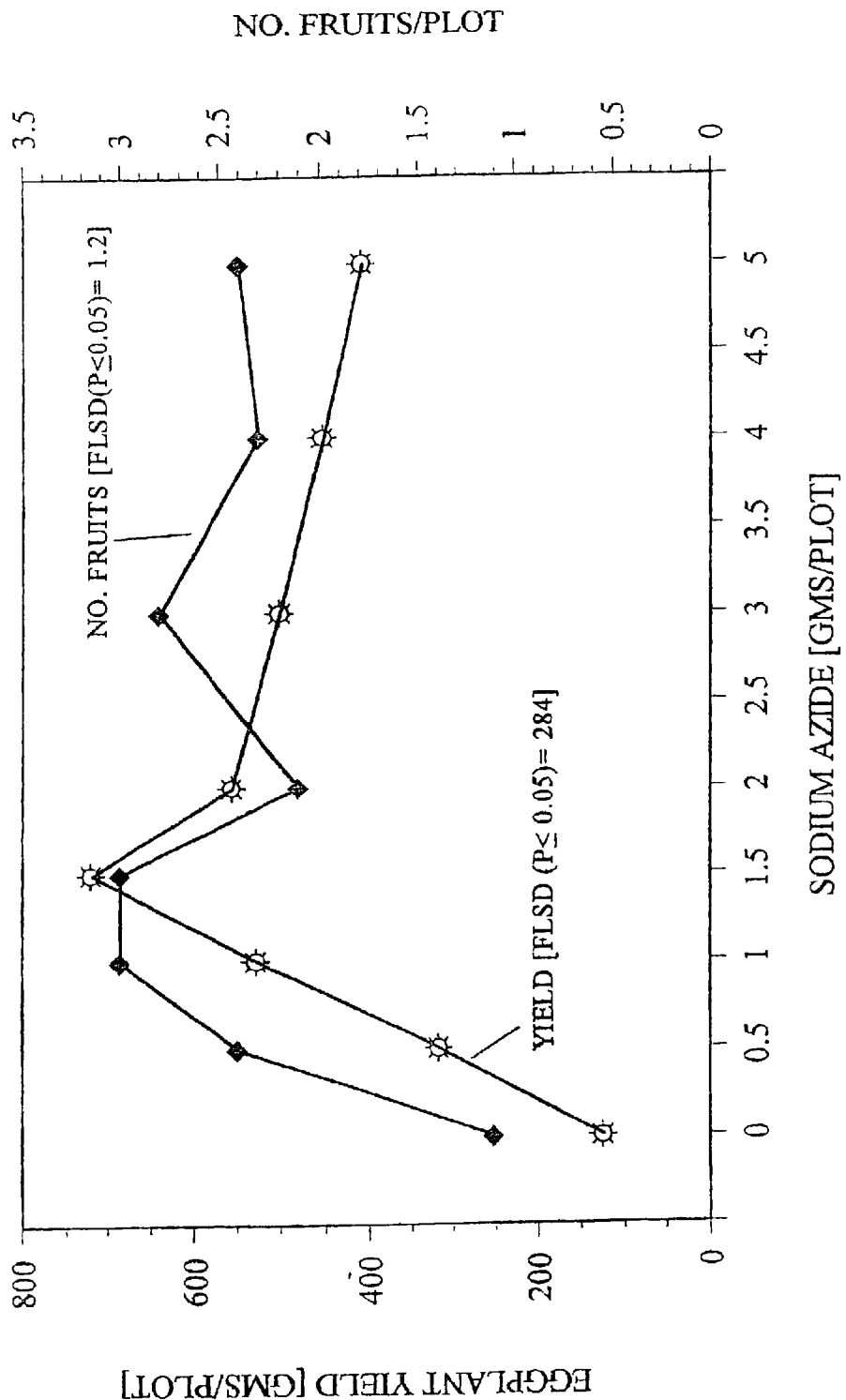
FIG. 1 is a graph illustrating the fruit yield of eggplants grown in soil treated with increasing doses of an aqueous solution of sodium azide.
Figure 2:
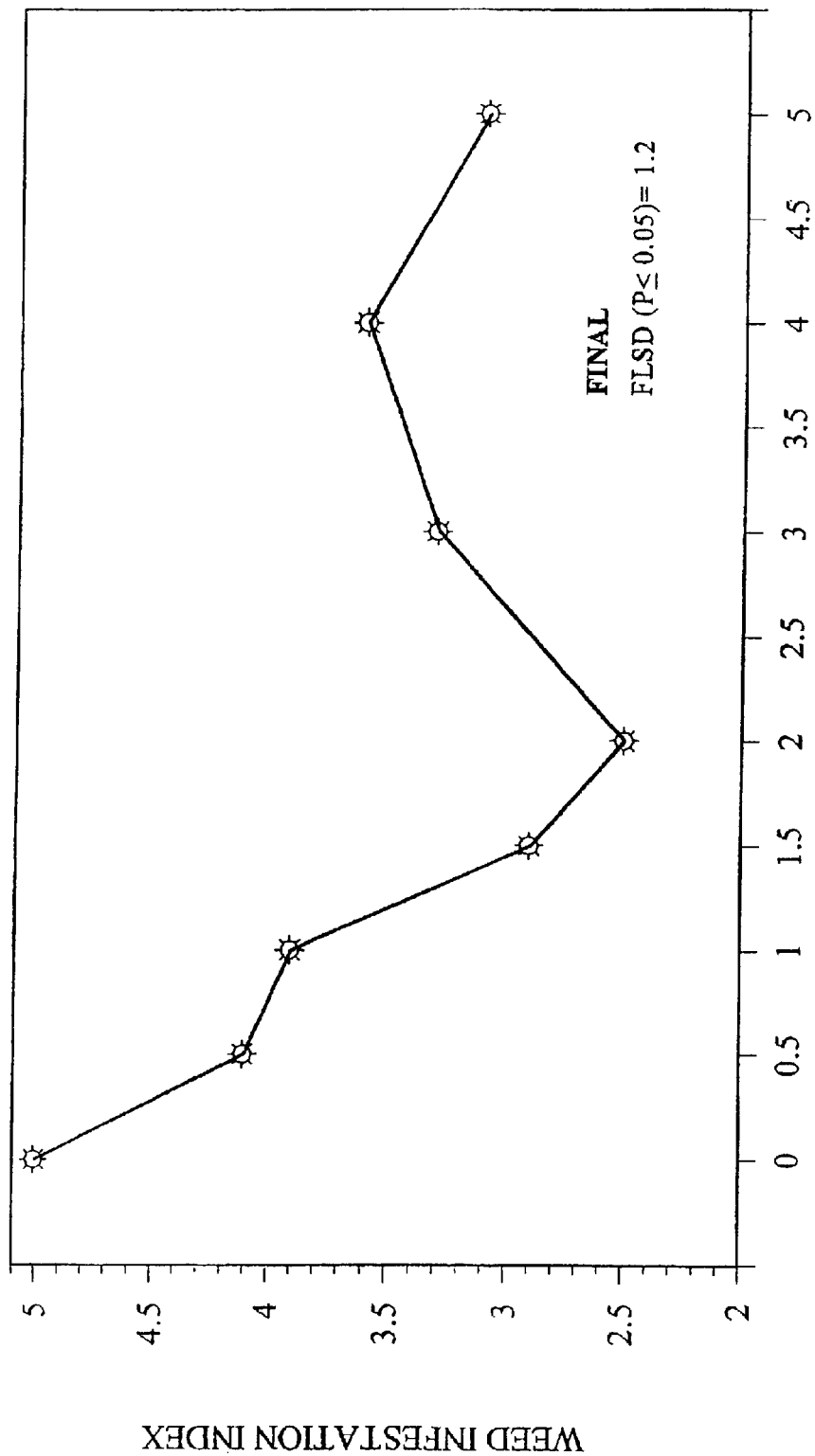
FIG. 2 is a graph illustrating the weed count or infestation in soil treated with increasing doses of an aqueous solution of sodium azide.
Figure 3:
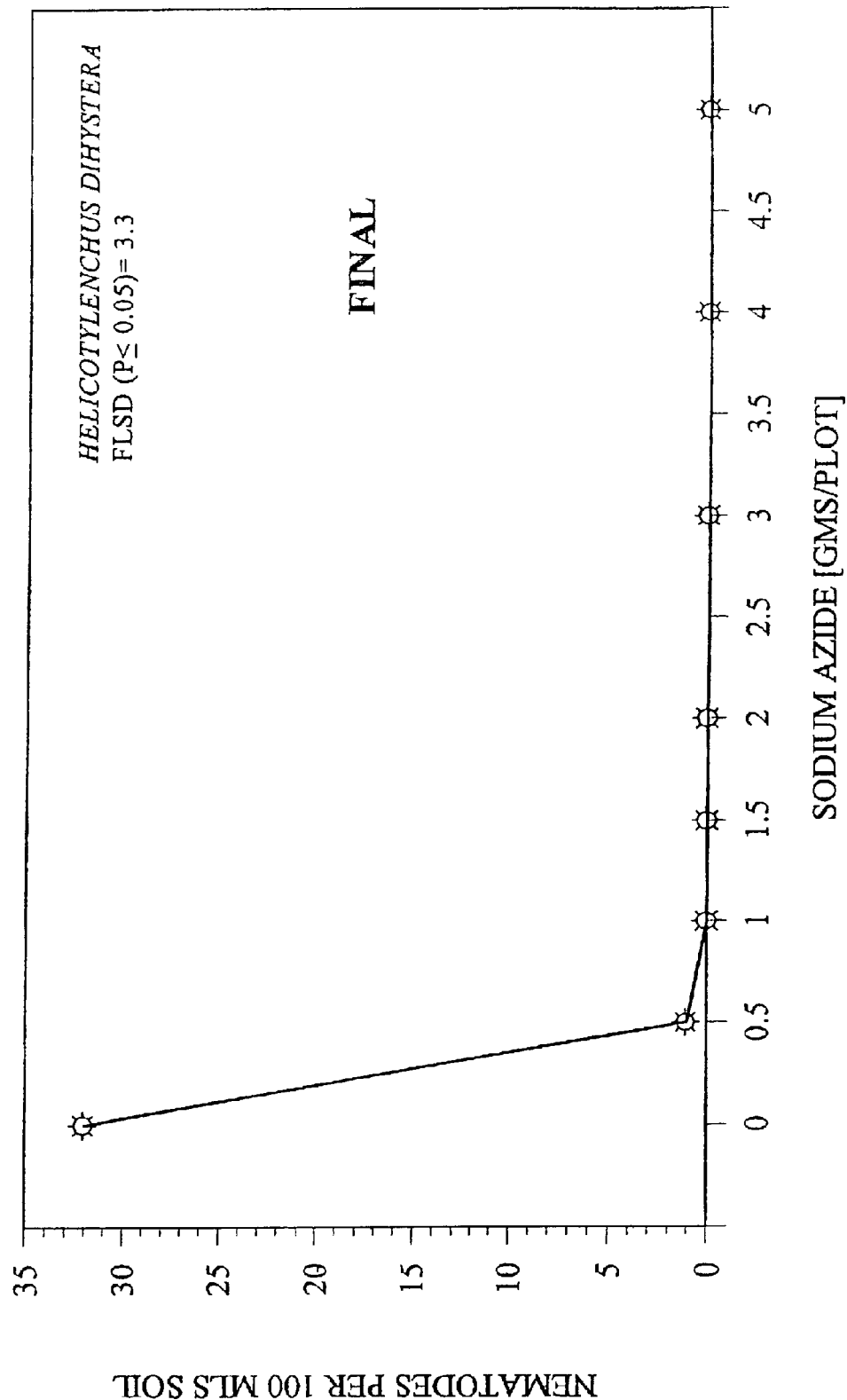
FIG. 3 is a graph illustrating the count of the nematode *Helicotylanchus dihystera* in soil treated with increasing doses of an aqueous solution of sodium azide.
Figure 4:
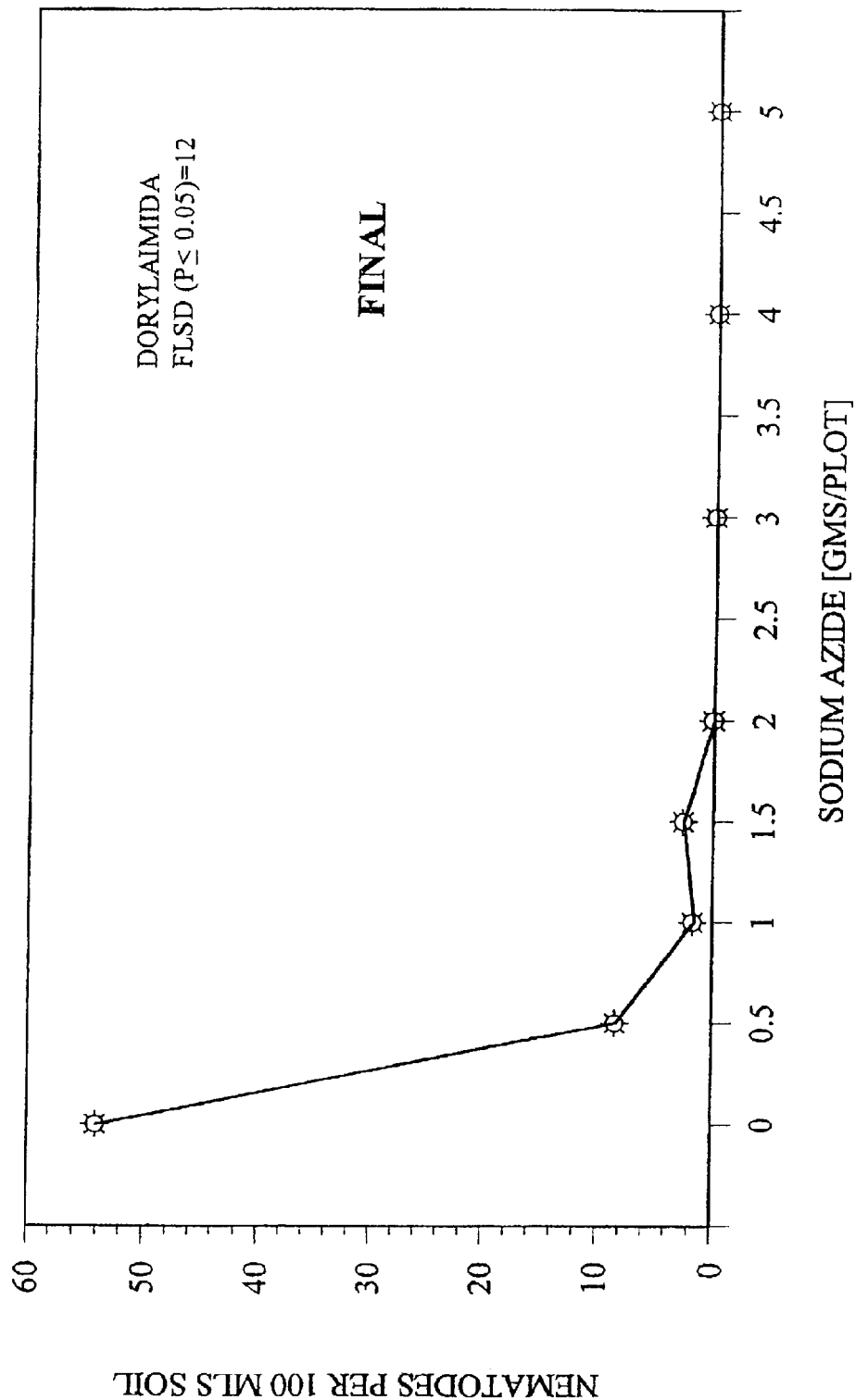
FIG. 4 is a graph illustrating the count of the nematode *Dorylaimida* in soil treated with increasing doses of an aqueous solution of sodium azide.

The present invention provides methods and compositions for controlling a population of a deleterious organism such as, but not limited to, an insect, a nematode or a weed or a combination thereof, by applying a composition comprised of a liquid medium, azide and amine. The liquid medium is both safe and stable for use in irrigation systems, such as in a drip irrigation line and may be used in formulations with plant nutrients and other pest control agents. The azide can be an ionic azide. Exemplary ionic azides include, but are not limited to, sodium and potassium salts or any combination thereof. The azide may be produced through the introduction of an azide salt to an aqueous medium. While sodium and potassium azides may be used most commonly, any azide salt, such as, for example, ammonium, calcium, zinc azides, are also appropriate. The compositions of the present invention provide effective nematocides having herbicidal properties, and do not cause significant or permanent harm to the environment.

Prior to application to the soil, care in handling is required to help assure that the azide component does not dissociate to form hydrazoic acid. Such dissociation can also prematurely occur after application to lower pH soils (e.g. <6–7) and in such applications, the presence of amines or pH buffering agents can help minimize or control the dissociation.

The term "controlling" as used herein refers to regulating a population of a deleterious organism that may be harmful to an agricultural product. The population may be regulated by the compositions and methods of the present invention so that the organism is killed, thereby reducing the viable populations such as by nematocidal, fungicidal, herbicidal or insecticidal activity or the like. The methods and compositions of the present invention may maintain and not allow a population of a deleterious organism to increase or may prevent an invasion of a soil by a deleterious organism.

The term "azide" as used herein refers to any compound having the $N_3^-$ moiety therein. The azide can be a metal azide wherein the metal is an alkali metal such as potassium, sodium, lithium, rubidium or cesium. The metal can be a transition metal such as, but not limited to, iron, cobalt, nickel, copper or zinc. It is understood that certain metallic azides can be formed in solution by mixing sodium azide or the like with a metallic salt such as, for example, copper sulfate. The azide of the present invention can also be an organic azide or ammonium azide. Some metal azides such as $Cu(N_3)_2$ and $Pb(N_3)_2$, are explosive and if such azides are used, precautions should be taken (e.g., that copper-containing fittings, such as brass or bronze, should not be used).

The term "amine" as used herein means an amine selected from group consisting of primary, secondary and tertiary aryl or alkyl amines, and mixtures thereof. Exemplary amines include ethanolamine, ethylamine butylamine, diethylamine, dimethylamine, phenylethylamine, alkanolamines (such as monoethanolamine, diethanolamine and diethylethanolamine), and mixtures thereof. The amine components of the compositions of the present invention can also provide an additional source of nitrogen for a crop planted in the soil. The amines should selected for compatability with a given application (e.g., melamine has limited solubility in water and is phytotoxic to a number of species).

Ethanolamine is most preferred in that it optimally enhances the azide's functionality by helping to prevent the azide from dissociating and forming hydrazoic acid prematurely. Prior to application (e.g., during manufacture, handling and other points prior to application), it is important that the azide be stabilized against such dissociation. Ethanolamine stabilization provides this pre-application stabilization, and importantly, does not impair the azide's efficacy when applied to the soil.

Further, ethanolamine desirably facilitates a measured diffusion of the azide in the soil from its point of application. Additionally, ethanolamine is readily biodegradable, which is an important attribute for any pesticide formulation ingredient.

The azide compositions of the present invention provide an amount of azide in the soil, which is effective for controlling a population of a deleterious organism therein. Preferably, the azide compositions contain up to about 40% (preferably about 10 to 20%) of azide (preferably sodium azide) and up to 10% (preferably of about 1 to 2%) of specified amine in an aqueous dispersal medium, said percentages being based upon the weight of said dispersal medium. Most preferably, the specified amine would be about 1 to 2% ethanolamine and the composition would further contain up to about 5% of detergent (most preferably about 0.01 to 0.5% of sodium lauryl sulfate).

The term "liquid medium" as used herein refers to an aqueous or organic fluid at least partially in the liquid phase under ambient conditions. Suitable fluids include, but are not limited to, water, an oil, an emulsion, a liquid organic compound such as, for example, ethanolamine, ethanol and the like.

The term "chelating agent" as used herein refers to any organic or inorganic compound that will bind to a metal ion having a valence greater than one, and includes, but is not limited to, organic chelating agents such as ethylenediaminetetracetic acid (EDTA), triethylene tetramine dihydrochloride (TRIEN), ethylene glycol-bis (beta-aminoethyl ether)-N,N,N',N'-tetracetic acid (EGTA), diethylenetriaminpentaacetic acid (DPTA), and triethylenetetramine hexaacetic acid (TTG), deferoxamine, Dimercaprol, edetate calcium disodium, zinc citrate, penicilamine succimer, Editronate or crown esters, cellulosic perivities, and any other chelating agent, salt or combination thereof, known to one of ordinary skill in the art, and which will chelate divalent metal ions such as, but not only $Ca^{2+}$, $Mg^{2+}$, $Mn^{2+}$, $Fe^{2+}$, and $Zn^{2+}$.

The term "pH buffering agent" as used herein refers to any organic or inorganic compound or combination of compounds that will maintain the pH of a solution to within about 0.5 pH units of a selected pH value. A "pH buffering agent" may be selected from, but is not limited to, Tris (hydroxymethyl) aminomethane (tromethaprim; TRIZMA base), or salts thereof, phosphates, amino acids, polypeptides or any other pH buffering agent or combination thereof.

The terms "detergent" or "surfactact" as used herein refers to an amphipathic compound, either neutral or ionic in nature, which is soluble in water, such as sodium lauryl sulfate which is preferred.

Sodium and potassium azides are typically first formulated as granules (attapulgite clay, diatomaceous earth) or they can be formed in a variety of liquid formulations. The stability of azide formulations is enhanced at pH levels of greater than about 8.7. For the control of pests such as nematodes and fungi such as *Armillaria, Verticillium*, and the protection of deep-rooted crops such as grapes, fruit, and nut trees, liquid formulations are preferred.

The delivery of an azide to a desired application zone may be difficult if the reactivity of the azide in the soil-air space and atmosphere is too rapid and results in an effective concentration of the active compound that is too low for pest control. The specified amines aid in increasing the effectiveness of the liquid medium in such conditions. Thus, the liquid medium can be modified depending upon the soil conditions in which the composition of the present invention is used such as, for example, by increasing the pH of the liquid medium for application to an acidic soil.

Aqueous azide solutions can be further enhanced in an alkaline solution by the addition of pH buffering agents such as, hydroxyl ions such as in the form of sodium or potassium hydroxide or the like, or by adding carbonates and phosphates. Some pH buffering agents may not be desired, however, when used with irrigation waters having, for example, a high calcium ion content. Calcium may combine with solubilized carbonates and/or phosphates of the compositions of the present invention to form calcium carbonate or phosphate precipitates that may corrode or clog irrigation systems. If precipitation is not a concern, any appropriate pH buffering agent may be used, such as, for example, ammonium, sodium or potassium phosphates, ammonium, sodium or potassium carbonates, ammonium, sodium or potassium citrates, acid-salt systems with pH buffering capacity, organic buffers such as Tris and the like, or hydroxyl ions that will maintain, either singly or in combination, a pH in the liquid medium of greater than about 8.7.

Suitable detergent can be added such as, but not limited to, sodium lauryl sulfate; Tween 20 [polyoxyethylene (20) sorbitan monolaurate]; Tween 40 [polyoxyethylene (20) sorbitan monopalmitate; Tween 40 [polyoxyethylene (20) sorbitan monopalmitate; Tween 60 [polyoxyethylene (20) sorbitanmonostearate; Tween 80 [polyoxyethylene (20) sorbitan monostearatepalmitate; Tween 85 [polyoxyethylene (20) sorbitan trioleate]; soaps, (i.e. salts of Na, K or ammonium and various fatty acids [ammonium oleate, potassium stearate, etc.]); and tergitol. By using a detergent, the liquid medium can be stabilized without the problem of forming calcium precipitates. The detergent may further cleanse an irrigation system that is used to apply a composition of the present invention to a soil. It is further contemplated to be within the scope of the present invention for the detergent to have wetting properties that may increase the dispersal of the composition of the present invention in the soil.

Additional additives useful in the present invention include amino acids, oligopeptides or a polypeptides. As used herein the terms "oligopeptide", "polypeptide" and "protein" refer to a polymer of amino acids of three or more amino acids in a serial array, linked through peptide bonds. The term "polypeptide" includes proteins, protein fragments, protein analogues, oligopeptides and the like. The term "polypeptides" further contemplates polypeptides as defined above that include chemically modified amino acids or amino acids covalently or noncovalently linked to labeling ligands. The amine groups can be in the form of a protein that can itself provide a pH buffering effect. For example, the protein casein can preferably be used. Casein is soluble in ethanolamine and, when added to soils, stimulates the activities of proteolytic microorganisms. The increased microbial proteolytic activity may further be antagonistic to plant parasitic nematodes and other soil borne pests. Suitable proteins for use in the compositions of the present invention include, but are not limited to, proteins derived from a cereal meal such as soybean meal, cottonseed meal, maize meal or wheat meal. Other suitable proteins can include zein, gluten, gelatin and the like or protein obtained from animal sources such as whey.

The azide formulations of this invention are preferably applied to the soil by drip irrigation. In other preferred embodiments, spray or other forms of soil application with subsequent soil tilling (i.e., after the azide is applied) is most desirable. Other conventional or suitable means of application can also be employed. The method of application is preferably selected to disperse a given azide formulation of this invention in the area containing the targeted deleterious organisms. Some pesticidal compositions, such as methyl bromide, are applied as gaseous phase fumigant that is injected into the soil in areas in which the crops are to be planted, but disperses broadly into the surrounding soil. The formulations of this invention are preferably applied as liquid formulations, by drip irrigation or spray application/rototill methods in pre-planting operations to utilize the selectivity of the azide formulation to particular deleterious organisms and to maximize the azide's contact with the soil regions in which these deleterious organisms are prevalent. In this manner, the extent of application can be more precisely controlled. For example, for a given soil type (e.g., sandy or clay type) the depth of penetration of a given quantity of applied aqueous formulation to the soil can be estimated or determined empirically and controlled to a significant degree. This is particularly advantageous in the practice of this invention, in that azide formulation can be applied to the upper zones of the crop area to eliminate or reduce the presence of weeds (e.g., nutsedge which has a root depth of 3–6 inch), without eliminating beneficial microorganisms which exist in deeper soil zones. Although the invention is not limited to the mechanism by which the azide functions, it is believed the azide can be absorbed into the root structure and the azide will then dissociate to form hydrazoic acid in the root.

Additionally, control of the depth of application allows the azide to remain present in those zones to which it was applied and allows for the reduction or elimination of azide from those zones by subsequent application of additional water (e.g., one of more subsequent drip or spray applications) to transport residual azide (e.g., azide not taken up by the weeds in the application zone) to lower depths in the soil. The remaining, lower concentrations of azide would control deleterious organisms in these lower regions, for which a lower concentration of azide would be sufficient, or indeed desirable, so as not to unduly impair beneficial organisms. As an example, in a pre-planting mode, the azide formulation can be applied to a depth of about 18 inches (e.g., the root depth of tomato plants) to control deleterious organisms that would otherwise interfere with tomato production, allowing uptake of azide by a deleterious plant's root system. The subsequent application of additional water would eliminate or minimize residual azide in this region of the soil, thereby not impacting the tomato plants.

The present invention is further illustrated by the following examples, which are provided by way of illustration and should not be construed as limiting.

EXAMPLE 1

Control of Nematodes and Weeds

In this example, the efficacy of pre-plant applications of $NaN_3$ for control of plant parasitic nematodes and weeds was studied in a microplot experiment using the aqueous formulation of the chemical. The formulation contained 5% sodium azide dissolved in demineralized water containing 0.5% sodium lauryl sulfate; final pH of the solution was 9.8. The square microplots of 1 ft$^2$ [929 cm$^2$] and 2 feet [61 cms] deep having an open-bottom were used. Each microplot was delimited by a terra-cotta chimney flue. The soil filling the plot was a sandy loam [pH=6.2; organic matter content <1.0%; C.E.C<10 meq/100 g soil] and was infested with the nematodes: *Meloidogyne incognita* [root-knot], *Paratrichodorus minor* [stubby root], *Tylenchorhynchus claytoni* [stunt], and *Helicotylenchus dihystera* [spiral]. Weeds introduced into the plots were principally crabgrass [*Digitaria sanguinalis*], yellow nutsedge [*Cyperus esculentum*], pigweed [*Amaranthus* spp.], and morning glories [*Ipomea* spp., *Jacquemontia tamnifolia*].

Applied to the plots was the aqueous formulation of $NaN_3$ diluted in irrigation water and delivered by drenching [2L/plot] at amounts of: 0, 0.5, 1.0, 1.5, 2.0, 3.0, 4.0, and 5.0 g sodium azide/plot. The plots were covered with standard polyethylene [1 mil] and after 10 days the cover was removed, the number of weeds was determined, soil samples for nematological analyses were taken and each plot was planted with two 3-week old 'Black Beauty' eggplant [*Solanum melongena*] seedlings. The plants were grown for 2 months and data were collected on yield, weed infestation and nematode populations. There were no nematodes in the planting time samples from plots treated with the solution of $NaN_3$ In contrast, soil from control plots were infested with all nematode species. When planted, there were no weeds in plots treated with all but the two lowest rates of $NaN_3$. Yield and number of fruits increased directly in response to $NaN_3$ rates from 0–1.5 g/plot and leveled out with no additional increases obtained in response to higher rates. At the end of the experiment there were no plant parasitic nematodes and no significant weed infestation in plots with the three highest rates of the chemical but there were significant populations of the parasites and weeds in plots treated with $\leq 2.0$ g $NaN_3$ rates. The results of Example 1 are illustrated in FIGS. 1–4.

EXAMPLE 2

Control of Root Knot

The value of $NaN_3$ solution for the suppression of the cotton wilt complex [*Fusarium oxysporum* f sp. *vasinfectum* x *Meloidogyne incognita*] was investigated in a greenhouse experiment with soil from a field having a severe wilt problem. The soil was apportioned in one kg amounts in 4 L plastic bags and was treated with an aqueous formulation of $NaN_3$ to have rates of: 10, 20, 30, 40, 50, 60, 70, 80, 90, and 100 mgs $NaN_3$/kg soil. The aqueous formulation was a solution containing 1% [w/v] $NaN_3$ in water containing 0.5% sodium lauryl sulfate with pH=9.8. After thorough mixing, the contents of a bag were poured into 1 L capacity, 10-cm-diam cylindrical plastic pots which were then covered with standard polyethylene [1 ml]. Each rate and the no treatment control was represented by 7 replications [pots] arranged in a randomized complete block design. Ten days after application of the chemical solution, the pots were uncovered and 5 seed of "Rowden" cotton [*Gossypium hirsutum*] were planted in each pot. The resulting plants were grown for 8 weeks. When the plants were removed after 8 weeks, soil samples were collected for nematological analyses. The shoots and roots of the plants were weighed and the root systems were examined and indexed for disease severity symptoms. Following examination, the roots were incubated to determine nematode populations.

Figure 5:
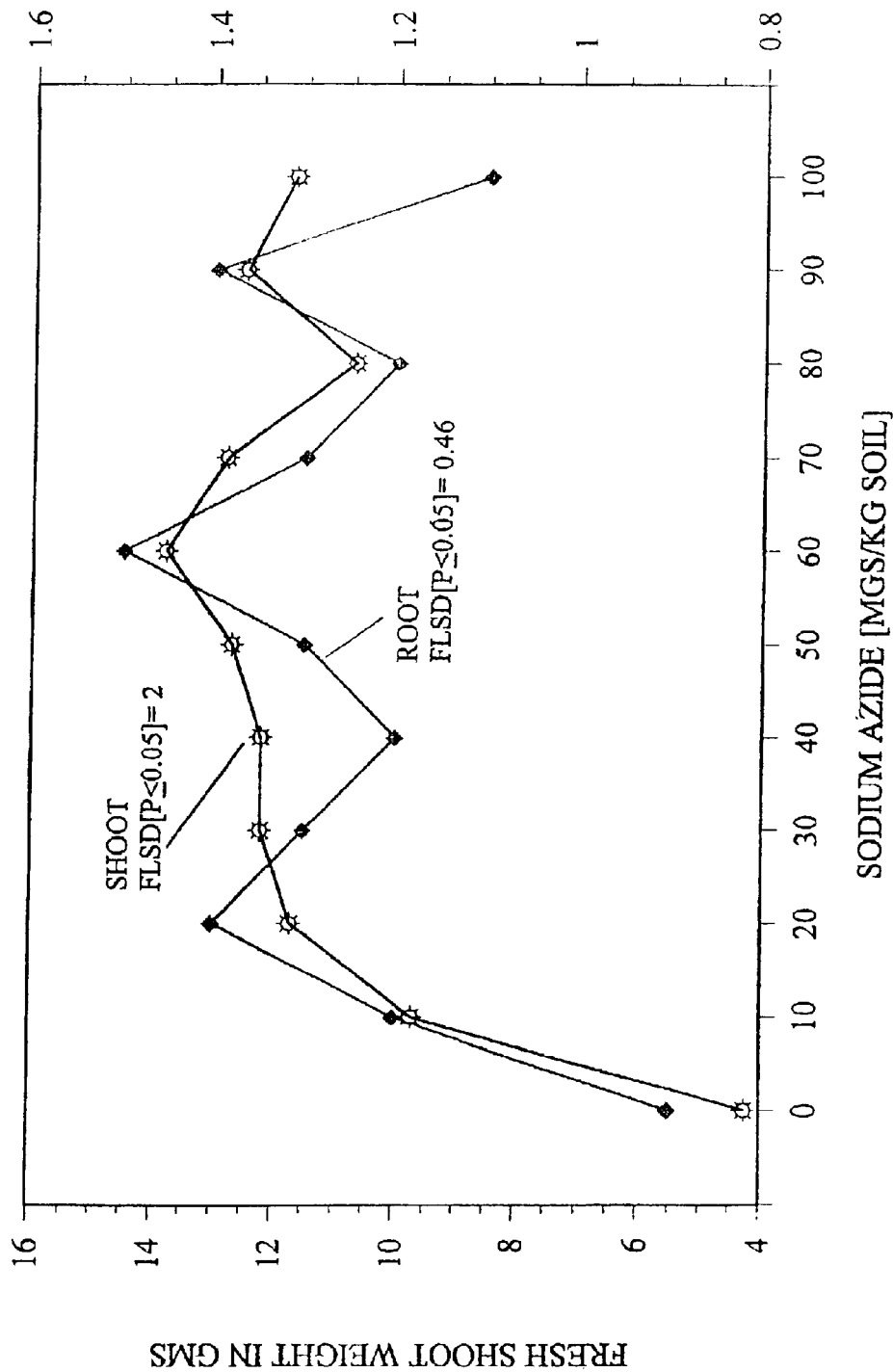
FIG. 5 illustrates a graph comparing both the fresh shoot weight and fresh root weight of cotton grown in soil treated with increasing doses of an aqueous solution of sodium azide.
Figure 6:
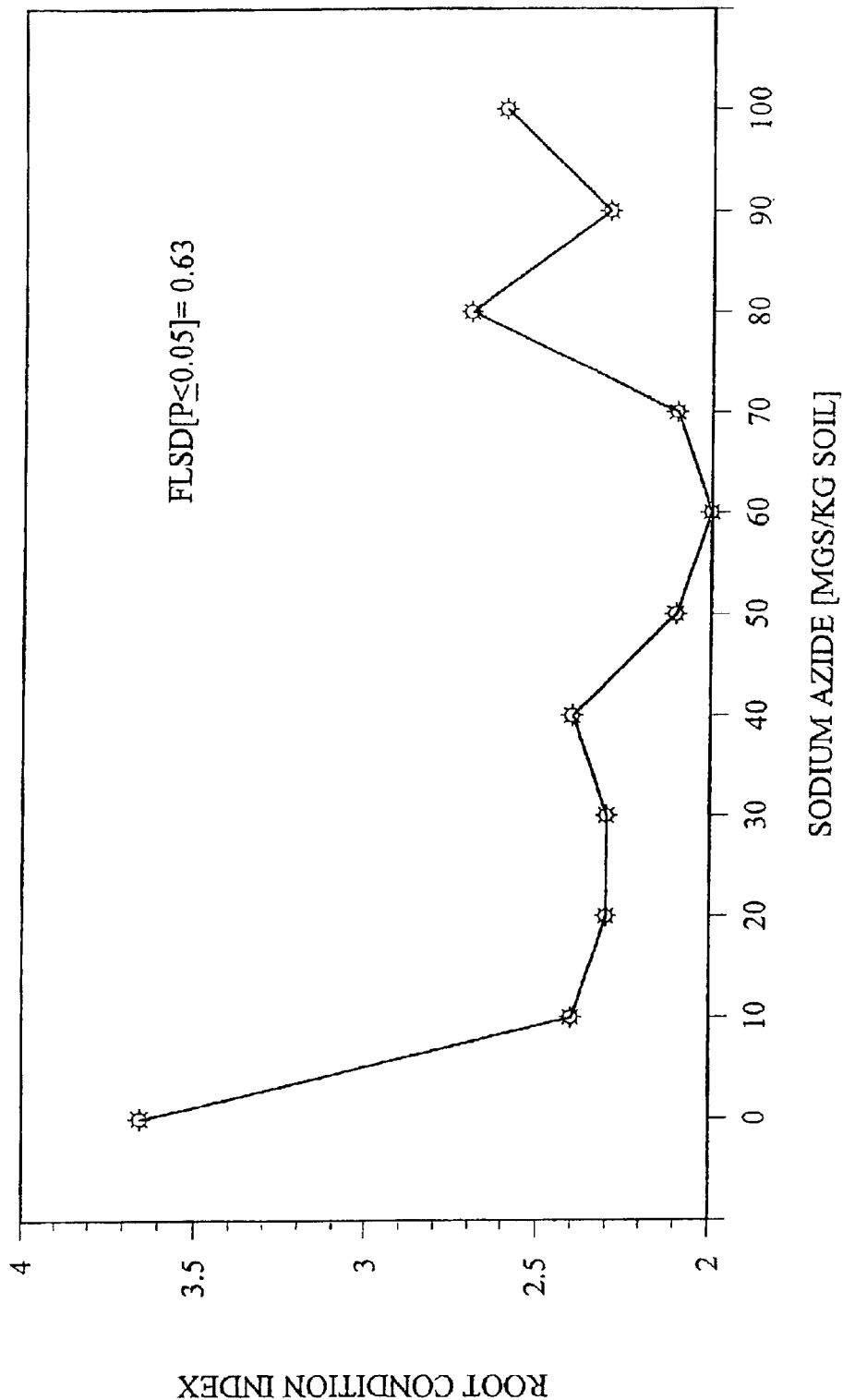
FIG. 6 is a graph illustrating the root condition index of cotton count of cotton grown in soil treated with increasing doses of an aqueous solution of sodium azide.

The results of the analysis indicated that at all $NaN_3$ dosages the plant parasitic nematodes were eliminated from the soil and roots. Sharp increases in weights of shoots and roots were recorded in response to $NaN_3$ application rates in the range 10–60 mgs/kg soil with no additional weight increments being obtained with rates $\geq 70$ mgs/kg soil. Cotton root health [root condition index] was markedly improved in response to all $NaN_3$ dosages; root systems of plants from pots with the 10 mg-rate were as healthy looking as those from pots treated with all other dosages of the compound. Results indicate that $NaN_3$ may be useful for suppression of Fusarium wilt complex and that rates required for wilt control are below those needed for broad-spectrum herbicidal activity. The results of Example 2 are further illustrated in FIGS. 5 and 6.

EXAMPLE 3
Amine-Protein Stabilizers in the Control of Nematodes and Weeds

This example illustrates the efficacy of pre-plant applications of an aqueous formulation of $NaN_3$ for control of plant parasitic nematodes and weeds in a microplot experiment with tomato [*Lycopersicon esculentum*]. $NaN_3$ was stabilized in the formulation by means of a mixture of amines and the commercially available protein, casein. The formulation contained 5% [w/v] $NaN_3$ dissolved in demineralized water containing 2% [v/v] of a 10% [w/v] casein solution in ethanolamine. Soil in the microplots was a sandy loam [pH=6.2; organic matter content<1.0%; C.E.C<10 meq/100 g soil] infested with the nematodes: *Meloidogyne incognita, Paratrichodorus minor, Tylenchorhynchus claytoni,* and *Helicotylenchus dihystera* 1]. Weeds in the plots were principally crabgrass [*Digitaria sanguinalis*], yellow nutsedge [*Cyperus esculentum*], pigweed [*Amaranthus* spp.], and morning glories [*Ipomea* spp., *Jacquemontia tamnifolia*].

$NaN_3$ was applied to the 1-ft$^2$ microplots by drenching [2 L/plot] at amounts of: 0, 0.5, 1.0, 1.5, 2.0, 3.0, 4.0, and 5.0 g/plot. The plots were covered with standard polyethylene [1 mil] tarp immediately after application of the chemical. After 10 days the cover was removed, the number of weeds was determined, soil samples for nematological analyses were taken and each plot was planted with two 4-week old 'Huskie' tomato seedlings. The plants were grown for 3 months and data were collected on yield, number of fruits, weed infestation and nematode populations.

Soil samples from plots treated with $NaN_3$ did not contain nematodes, but the soil samples from the control plots had significant numbers of all nematode species. At planting time, there were no weeds in plots treated with all but the three lowest rates of $NaN_3$. Yield and number of fruits increased directly in response to $NaN_3$ rates from 0–4 g/plot. At the end of the experiment there were no plant parasitic nematodes in $NaN_3$-treated plots for all rates of application.

Figure 7:
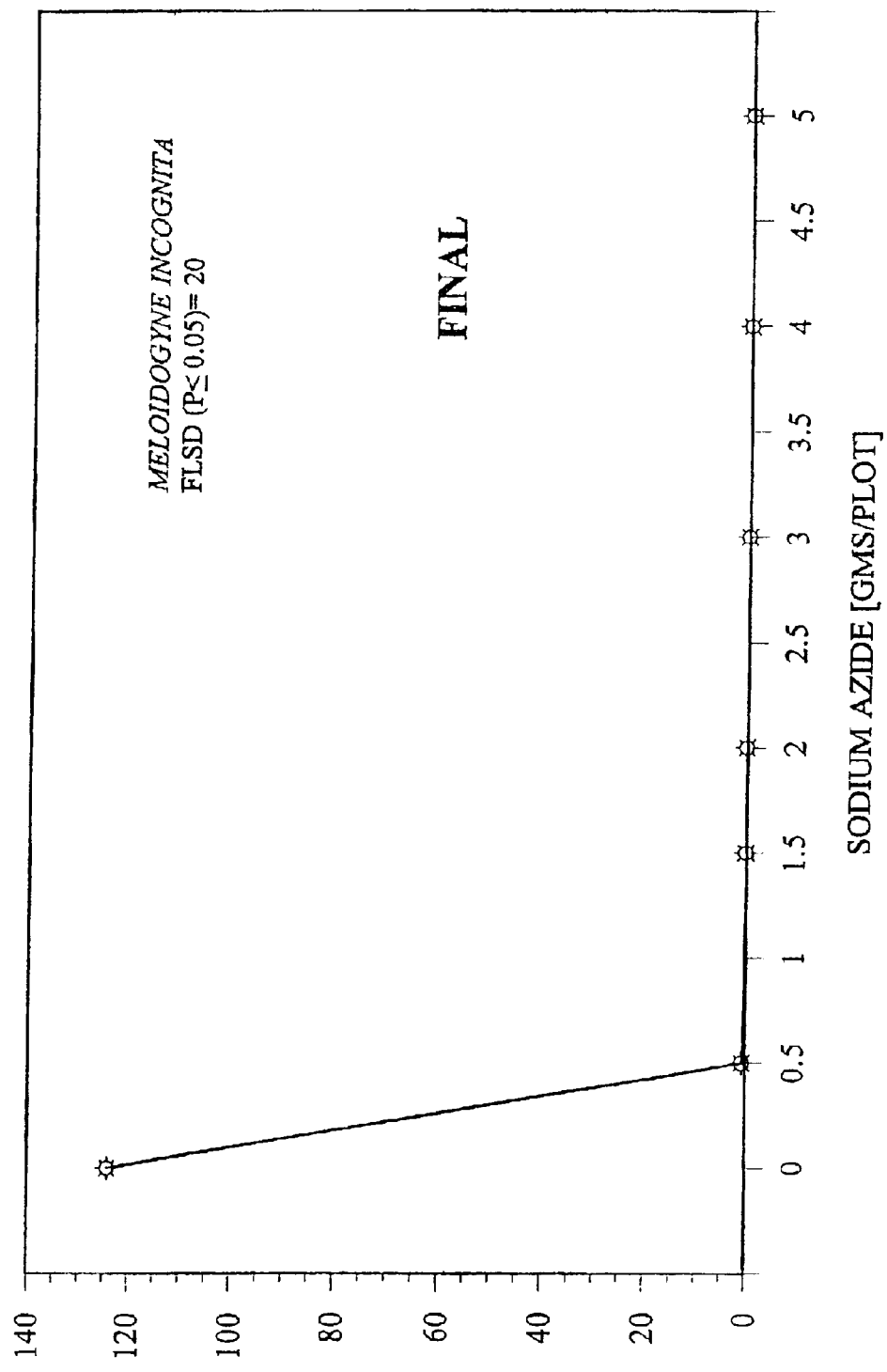
FIG. 7 depicts a graph illustrating the count of the nematode *Meloidogyne incognita* in soil treated with increasing doses of an aqueous solution of sodium azide in a mixture of amines and proteins.
Figure 8:
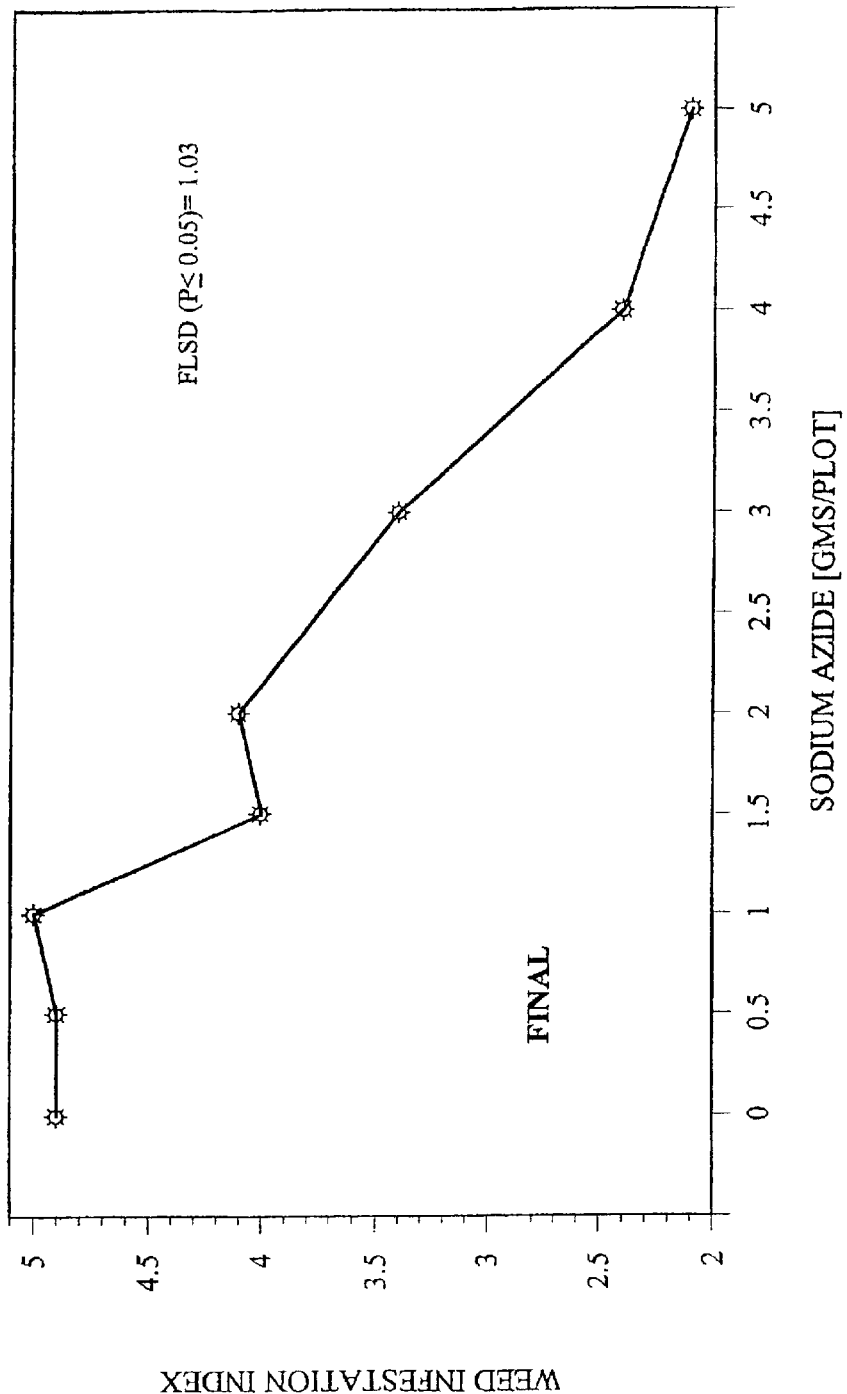
FIG. 8 is a graph illustrating the weed count or infestation in soil treated with increasing doses of an aqueous solution of sodium azide in a mixture of amines and proteins.
Figure 9:
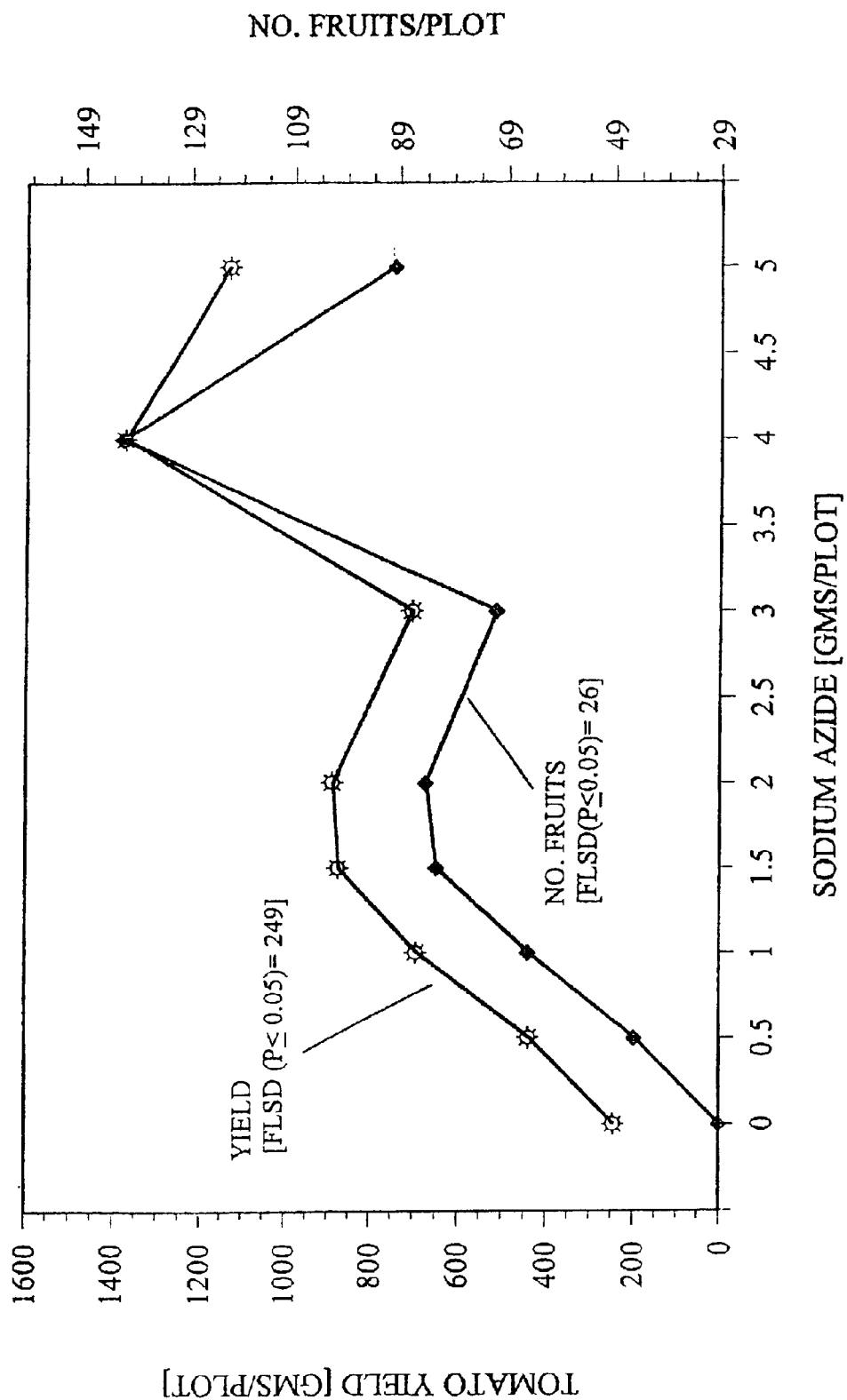
FIG. 9 depicts a graph comparing the number of fruits and yield of tomato plants grown in soil treated with increasing doses of an aqueous solution of sodium azide in a mixture of amines and proteins.

Final weed counts were inversely related to $NaN_3$ rate in a pattern described [$R^2=0.95**$] by W=−0.32x+5.82, where W represents total weed population density/microplot and X, azide rates in gms $NaN_3$/plot. Results indicate that the amine-protein formulation is superior for nematode control and equal in herbicidal activity to formulations stabilized with inorganic buffers. The data also suggest that it is possible to deliver $NaN_3$ into soil together with organic compounds that can serve as plant nutrients and stimulate beneficial soil microbial activities. The results of Example 3 are illustrated in FIGS. 7–9.

EXAMPLE 4

Control of Root-Knot Nematode and Weeds in Green Peppers and Tomatoes

This example illustrates the efficacy of pre-plant applications of $NaN_3$ for control of root-knot nematode [*Meloidogyne incognita*], coastal bermudagrass [*Cynodon dactylon*], yellow nutsedge [*Cyperus esculentum*] and other weeds in pepper [*Capsicum annum*] and tomato [*Lycopersicon esculentum*] growth. The soil was a calcareous silty clay loam with pH 7.8 and <1% organic matter. The $NaN_3$ was applied at drenching rates of 100 and 200 kg/ha using a solution of sodium azide in sodium lauryl sulfate. Each dosage rate was delivered into pre-acidified soil as well as in non-acidified and administered using 3 different water levels: 3, 10, and 15 L/m$^2$. Acidification was with $H_2SO_4$ to lower soil pH to less than 7.00. The soil was covered with standard polyethylene tarp immediately after $NaN_3$ application. After 3 weeks the soil was uncovered and a soil sample was removed for nematological analyses and the weeds were counted. Tomato and pepper seedlings were then transplanted 6 weeks after $NaN_3$ application.

Azide applications effectively controlled greater than 90% of the nematodes and all weeds at dosages of 100 and 200 kgs. The compound was particularly effective against nutsedge. $NaN_3$ performed well when drenched with any of the 3 water levels. There was no evidence of phytotoxicity to pepper or tomato plants in any of the plots treated with $NaN_3$.

EXAMPLE 5
Nematicidal and Herbicidal Properties of Potassium Azide

In this example, the nematotoxic properties of liquid potassium azide $KN_3$ are illustrated using soil from a cotton field infested with the reniform nematode (*Rotylenchulus reniformis*). The liquid potassium azide compound was added to the soil in an aqueous solution of amounts of: 1, 2, 3, 4 and 5 mgs $KN_3$ per kg of soil. The formulation used for this experiment was 1% $KN_3$ and 0.5% sodium lauryl sulfate. Soil samples were collected one week after the application of the $KN_3$ solution for nematological analysis using such techniques as the salad bowl incubation technique. From the analysis it was shown that the numbers of reniform nematode declined exponentially in response to the increasing $KN_3$. Rates of 4–5 mg of $KN_3$ per kg of soil showed an almost 100% control of the reniform nematodes. Numbers of microbivorous nematodes declined in an almost linear fashion in response to the increasing dosages of $KN_3$.

In the application of $KN_3$ rates of 20–200 mg/kg of soil applied to a soil infested with crab grass (*Digitaria sanguinalis*), purple nutsedge (*Cyperus rotundus*), Jimson weed (*Datura stramonium*) and a variety of other weeds resulted in the number of weeds declining in proportion to rates used. Rates of greater than 140 mg/kg of soil resulted in over 80% control rates for weeds.

While specific embodiments have been set forth as illustrated and described above, it is recognized that variations may be made with respect to disclosed embodiments. Therefore, while the invention has been disclosed in various forms only, it will be obvious to those skilled in the art that many additions, deletions and modifications can be made without departing from the spirit and scope of this invention, and no undue limits should be imposed except as set forth in the following claims.

What is claimed is:

1. A composition for controlling a population of a deleterious soil organism comprising: an azide selected from the group consisting of alkali metal and ammonium azides, and combinations thereof; and at least about 1% by weight of an amine selected from group consisting of ethylamine ethanolamine, butylamine, diethylamine, dimethylamine, phenylethylamine, alkanolamines, diethanolamine, diethylethanolamine, and mixtures thereof.

2. The composition of claim 1, further comprising a dispersal medium.

3. The composition of claim 2, wherein the dispersal medium is a liquid medium.

4. The composition of claim 3, wherein the liquid medium contains water.

5. The composition of claim 2, wherein the dispersal medium is a solid dispersal medium.

6. The composition of claim 1, wherein the azide is an alkali metal azide selected from the group consisting of potassium azide, sodium azide, lithium azide, and combinations thereof.

7. The composition of claim 1, wherein the azide is ammonium azide.

8. The composition of claim 1, wherein the composition further comprises one or more detergents, pH buffering compounds, alkalis, amino acids, oligopeptides, polypeptides and combinations thereof.

9. The composition of claim 8, wherein the detergent is selected from the group consisting of Tween 20 (polyoxyethylene (20) sorbitan monolaurate); Tween 40 (polyoxyethylene (20) sorbitan monopalmitate); Tween 60 (polyoxyethytene (20) sorbitan monostearate); Tween 80 (polyoxyethylene (20) sorbitan monostearate palmitate); Tween 85 (polyoxyethylene (20) sorbitan trioleate), tergitol, sodium lauryl sulfate and combinations thereof.

10. The composition of claim 2, wherein the azide comprises up to about 40% and the amine comprises up to about 10%, each based upon the weight of said dispersal medium.

11. The composition of claim 10, wherein the azide comprises up to about 20% and the amine comprises up to about 2% based upon the weight of said dispersal medium.

12. The composition of claim 11, wherein the azide is sodium azide and the amine is ethanolamine.

13. The composition of claim 12, further comprising sodium lauryl sulfate.

14. The composition of claim 13, comprising up to about 20% of sodium azide, up to about 2% of ethanolamine and up to about 0.5% of sodium lauryl sulfate, each based upon the weight of said dispersal medium.

15. A composition for controlling a population of a deleterious soil organism comprising: an aqueous liquid medium; azide salt selected from the group consisting of sodium azide and potassium azide; and at least about 1% by weight of an amine selected from group consisting of ethylamine ethanolamine, butylamine, diethylamine, dimethylamine, phenylethylamine, alkanolamines, diethanolamine, diethylethanolamine, and mixtures thereof.

16. The composition of claim 15, further comprising additive selected from the group consisting of detergents, pH buffering agents, alkalis, amino acids, oligopeptides, polypeptides and combinations thereof.

17. A method of controlling a population of a deleterious soil organism, in soil, comprising the step of: applying to a soil a composition comprising an azide selected from the group consisting of alkali metal and ammonium azides, and combinations therof, a liquid medium, and at least about 1% by weight of an amine selected from group consisting of ethylamine ethanolamine, butylamine, diethylamine, dimethylamine, phenylethylamine, alkanolamines, diethanolamine, diethylethanolamine, and mixtures thereof, wherein the amount of azide in the soil is effective for controlling a population of a deleterious organism therein.

18. The method of claim 17, wherein the amount of azide in the soil effective for controlling the population of a deleterious organism therein is in the range of about 1 to about 200 mg per kg of soil.

19. The method of claim 18, wherein the azide is selected from the group consisting of sodium azide and potassium azide, and the amine is selected from the group consisting of ethanolamine, dimethylamine, ethylamine, butylamine, diethylamine, diethanolamine, and phenylethylamine.

20. The method of claim 19, wherein the composition further comprises additive selected from the group consisting of detergents, pH buffering agents, alkalis, amino acids, oligopeptides, polypeptides and combinations thereof.

21. The method of claim 20, wherein the azide is sodium azide, the amine is ethanolamine and the detergent is sodium lauryl sulfate.

22. The method of claim 21, comprising up to about 20% sodium azide, up to about 2% ethanolamine and up to 0.5% sodium lauryl sulfate, each based upon the weight of the liquid medium which is applied.

23. The method of claim 17, wherein the azide is an alkali metal azide selected from the group consisting of potassium azide, sodium azide, lithium azide, and combinations thereof.

24. A method for delivering a pesticidal composition comprising: applying to soil a pesticidal composition, prior to planting, to the areas of the soil in which the plant's root are to grow, wherein the pesticidal composition comprises an aqueous liquid medium, azide selected from the group consisting of potassium azide and sodium azide, and at least about 1% of an amine selected from group consisting of ethylamine ethanolamine, butylamine, diethylamine, dimethylamine, phenylethylamine, alkanolamines, diethanolamine, diethylethanolamine, and mixtures thereof.

25. The method of claim 24, in which the applying is by drip irrigation.

26. A kit for preparing a pesticidal composition comprising packaging and having therein an azide selected from the group consisting of alkali metal and ammonium azides, and combinations thereof, at least about 1% by weight of an amine selected from group consisting of ethylamine ethanolamine, butylamine, diethylamine, dimethylamine, phenylethylamine, alkanolamines, diethanolamine, diethylethanolamine, and mixtures thereof, and instructions for preparing the pesticidal composition and applying the pesticidal composition to a soil, thereby reducing a population of deleterious organisms therein.

27. The kit of claim 26, further comprising a dispersal medium, wherein the dispersal medium is a liquid medium.

* * * * *

UNITED STATES PATENT AND TRADEMARK OFFICE
CERTIFICATE OF CORRECTION

PATENT NO. : 6,932,985 B2
APPLICATION NO. : 10/268050
DATED : August 23, 2005
INVENTOR(S) : Rodrigo Rodriguez-Kabana It is certified that error appears in the above-identified patent and that said Letters Patent is hereby corrected as shown below:

At column 1, line 8, after "2001" please insert -- , --.

At column 8, line 18, after "$NaN_3$" please insert -- . --.

At column 11, line 13, please delete "(polyoxyethytene" and insert -- (polyoxyethylene --, therefore.

At column 11, line 47, please delete "therof," and insert -- thereof, --, therefore.

Signed and Sealed this

Twenty-fourth Day of July, 2007

JON W. DUDAS
*Director of the United States Patent and Trademark Office*